United States Patent [19]
Larsen

[11] 3,952,196
[45] Apr. 20, 1976

[54] RADIATION DETECTION APPARATUS
[75] Inventor: Theodore E. Larsen, Edina, Minn.
[73] Assignee: Detector Electronics Corporation, Minneapolis, Minn.
[22] Filed: Feb. 5, 1975
[21] Appl. No.: 547,173

[52] U.S. Cl. .............................. 250/372; 250/578; 340/401
[51] Int. Cl.² ......................................... G01J 1/42
[58] Field of Search ............. 324/51; 250/578, 372, 250/373; 328/6; 340/227 R, 401 S

[56] References Cited
UNITED STATES PATENTS

| | | | |
|---|---|---|---|
| 2,096,323 | 10/1937 | Gille | 250/578 |
| 3,105,908 | 10/1963 | Burkhardt et al. | 250/372 |
| 3,387,135 | 6/1968 | Engh | 328/6 |
| 3,510,648 | 5/1970 | Leger | 250/301 |
| 3,654,477 | 4/1972 | Benjamin | 250/552 |
| 3,700,909 | 10/1972 | Murray | 250/562 |
| 3,774,039 | 11/1973 | Price | 250/552 |
| 3,842,263 | 10/1974 | Kornrumph et al. | 250/552 |

Primary Examiner—Harold A. Dixon
Attorney, Agent, or Firm—James R. Cwayna

[57] ABSTRACT

A device for determining that the optical surfaces through which radiation must travel from a hazardous area of radiation to a radiation detector are free from radiation absorbing material or radiation blocking material, the device including an enclosure for commonly housing both a source of and a detector of radiation while isolating the same from each other, preventing radiation transmission within the housing from the source to the detector, such enclosure defining a path for radiation emission from the source outwardly from the housing to a reflective surface or surfaces which surface or surfaces will redirect the radiation back to the detector through the same optical surfaces that radiation from the hazardous area must pass. The relective surface or surfaces may be integral with the enclosure or may be remotely located therefrom.

14 Claims, 4 Drawing Figures

RADIATION DETECTION APPARATUS

FIELD OF THE INVENTION

This invention relates to devices for determining that the optical path over which a hazardous area is being monitored by a radiation detector is free of radiation blocking or radiation absorbing material.

The optical path is defined and related to the optical surfaces through which radiation must pass for detection by the detecting device.

The invention is also particularly related to but not limited to the detection of ultraviolet radiation as may be caused by a fire.

BACKGROUND AND OBJECTS OF THE INVENTION

Radiation detection apparatus has many useful applications.

Ultraviolet radiation detectors are useful as fire detectors in various applications. In most applications, detectors capable of UV detection are directed towards the area of possible hazard and these detectors will respond to UV radiation transmitted over any unobstructed path from these areas. Obviously, it is necessary that these detectors be in condition to receive the UV in order to respond thereto and it is very important that the same be periodically tested to determine whether or not their radiation transmitting components are capable of transmitting radiation and whether or not the unit is capable of responding to the radiation that is transmitted from a fire.

This invention relates to an enclosure for a device which is best utilized for automatically determining whether or not the surfaces through which radiation must pass are free from radiation blocking or obstructing material.

The optical surfaces of a UV detection device include not only the surface of the UV detector through which radiation enters the sensing area but also include any components such as lenses, windows or the like which may be placed in front of the detector. Many installations require such additional components for various reasons and all optical surfaces must be considered for proper functioning of the detection device. Many different materials may accumulate on these optical surfaces and some of these materials could adversely affect the transmission of radiation from the hazardous area to the detector.

To overcome these problems, while providing a device that will not require a manual exposure of the detector to UV such as is often done by directing a source of UV at the detector from a point external to the detector, applicant has provided a device that will provide for monitoring of the otpical surfaces of the detector by the transmission of the UV radiation from a UV source to a reflective surface or surfaces that will direct UV back to the detector unit through the same optical surfaces that UV radiation from a fire must pass in order to allow the detector to respond to the fire.

It is therefore an object of applicant's invention to provide a device for the detection of radiation which will, in addition to detecting such radiation, monitor the optical surfaces through which the radiation must pass to insure the absence of radiation absorbing or blocking materials.

It is a further object of applicant's invention to provide a device for the detection of ultraviolet radiation from a fire which will also monitor the optical surfaces of the detector unit to insure the absence of ultraviolet absorbing or blocking materials.

It is a further object of applicant's invention to provide an enclosure for commonly housing a source of ultraviolet radiation and a detector of ultraviolet radiation while maintaining such source and detector in UV optically isolated relation to each other.

It is a further object of applicant's invention to provide an enclosure for a source of ultraviolet radiation and a detector for such radiation with means for directing radiation from such source outwardly from the enclosure and means for reflecting the outwardly directed radiation back to the detector through the same optical surfaces that the radiation from a monitored area would pass.

It is still a further object of applicant's invention to provide a detection unit for minitoring the optical surfaces through which ultraviolet radiation from a source such as a fire must be transmitted for the detection unit to respond.

These and other objects and advantages of the applicant's invention will more fully appear from the following disclosure made in connection with the accompanying drawings in which the same numerals are utilized to designate the same or similar parts throughout the several views, and in which.

The detection unit as illustrated and discussed hereinafter is useful for the detection of various forms of radiation such as ultraviolet or infrared. The description is directed to ultraviolet detection and the unit is described as a fire detector.

In accordance with the accompanying drawings, the source and detector unit of applicant's invention is generally designated 11.

Figure 1:
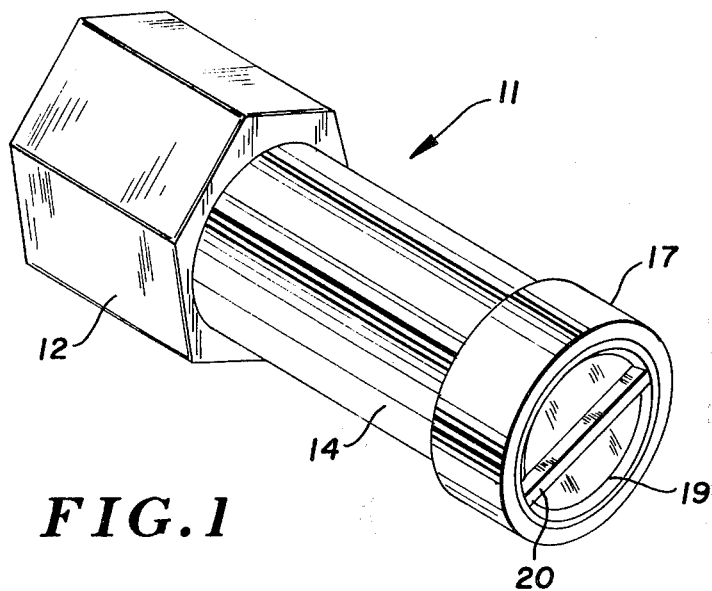
FIG. 1 is a perspective view of a source and detection unit embodying the concepts of applicant's invention.
Figure 2:
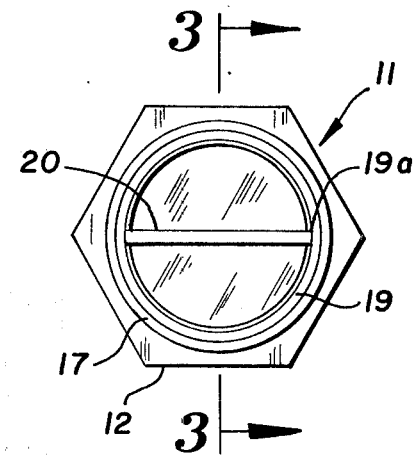
FIG. 2 is an end view of the source and detector unit shown in FIG. 1.

As illustrated and in the form shown in FIG. 2, the source and detector unit 11 includes a first mounting portion 12 arranged to position a mounting plate 12a upon which the required UV source and UV detectore units are placed. The mounting portion 12 is arranged for attachment to an appropriate surface for direction at the area to be monitored for UV radiation due to a fire or radiation from any other UV source. The means for attaching the mounting portion 12 is not shown.

The ultraviolet source S and the ultraviolet detector D are positioned on plate 12a. Such devices are commercially available and further description thereof should not be necessary.

Figure 3:
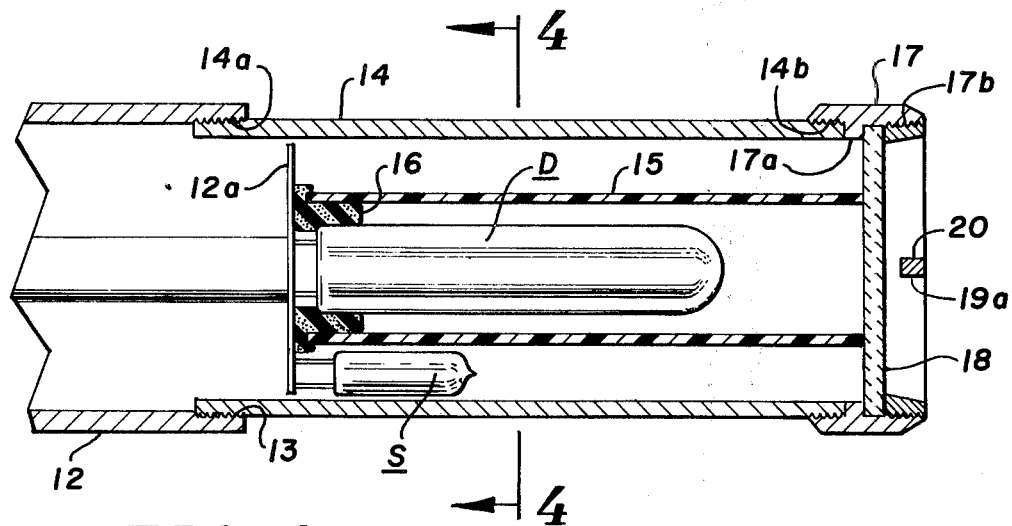
FIG. 3 is a vertical section taken substantially along Line 3—3 of FIG. 2.
Figure 4:
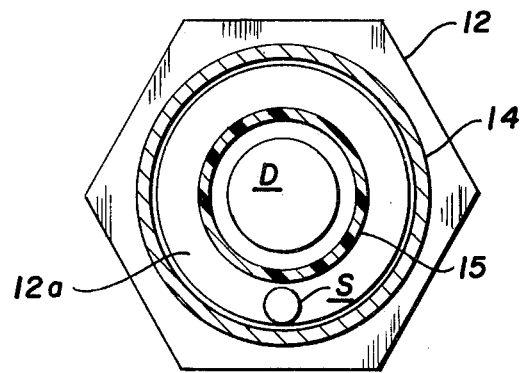
FIG. 4 is a transverse section taken substantially along Line 4—4 of FIG. 3.

As illustrated in FIG. 3, the mounting portion 12 is provided with an inwardly threaded and inwardly directed area 13 to receive an externally threaded, longitudinally extending housing member 14. A stop shoulder 14a is provided to abut with mounting portion 12.

An internally arranged, optically appropriate shielding member 15 is arranged about the detector unit D to shield the same from the radiation provided by source S. Throughout this disclosure, the terminology "optical" is utilized and radiation passing is utilized to describe various of the surfaces. An optical or radiation passing surface is defined as a surface that will permit the passage of radiation to which the detection unit is sensitive while a shielding surface or shielding member is defined to be capable of absorbing and not transmitting radiation in the range of sensitivity of the detector unit. The shielding member 15 is classified as an optical shielding member and though the same may be capable of transmitting visible radiation, it is not capable of transmitting radiation in the range of sensitivity of the detector.

The shielding member 15 extends longitudinally in housing 14 and is arranged to abut with mounting plate 12a, and a resilient, optical shielding member 16 may be interposed therebetween and extend longitudinally about detector D to insure a radiation seal at this juncture. The resiliency of member 16 serves a dual purpose. The shielding member 15 will be self-centering about the detector D and will assist in providing the radiation seal on the opposite end of shielding member 15 as is discussed hereinafter.

The housing portion 14 is provided with an externally threaded portion 14b on the opposite end thereof; this portion arranged to receive a threaded cap or closure member 17 thereabout. As illustrated, this closure member 17 is provided with a radially inwardly directed shoulder 17a to abut with the end of housing 14 and seal thereagainst.

An optical or radiation passing surface, hereinafter termed a lens 18 is positioned against shoulder 17a and is held in place thereagainst by a bezel 19 threadably received into a longitudinally extending, internally threaded portion or extension 17b of closure member 17.

The relationship of the length of housing 14, length of shielding member 15, resilient member 16 and the closure member 17, lens 18 and bezel 19 provides a radiation seal of the lens 18 to the shielding member 15 such that two distinct radiation passages exist through lens 18.

It should be obvious that this radiation seal may be provided between the source S and the detector D at the lens area through various means. The lens 18 and the shielding member could be physically joined through glueing or similar operations but the primary concept is the isolation of the source S from the detector D such that the radiation from the source S must pass from the housing before its reflection to the detector D.

As stated, two radiation passages exist. The first of such passages is defined by the interior of housing 14 and the exterior of the shielding member 15; the second such passage being defined by the interior of the shielding member 15. As stated, a radiation shield is provided by the cooperative arrangement of the lens 18 and the shielding member 15 and therefore it should be obvious that for communication of the radiation, in the sensitive range of the detector, the same must pass outwardly through lens 18 from the first passage and be reflected back through lens 18 into the second passage. This reflection may, in a very simple form be achieved by reflecting from the surface of the bezel 19. The main aspect being that the radiation must pass outwardly through the lens 18 or more importantly, from the housing, to some reflective surface.

One further consideration should be made when dealing with the concept of the radiation passages. It is not necessary, nor a limiting aspect of the invention, to state that the radiation emission is provided in the first passage and that the detector is arranged within the second passage as this is purely a matter of choice.

Applicant has also provided, in a modified form of the invention, a means for mounting a reflective member 20 on the bezel 19 in slightly spaced relation to the lens 18. In the form shown, this reflective member 20 is provided to extend entirely across the lens and be captured in diametrically opposed slots 19a on the bezel 19. In this manner, the reflective member 20 is disposed in spaced relation from the lens 18. The concept of so disposing this refective member 20 includes the concept of remotely locating this reflective surface with respect to the housing.

A basic concept of applicant's invention is to insure that the various surfaces for the transmission and reception and thus detection of radiation are in condition to pass radiation. If the lens or any other surface will not allow the transmission of radiation from the source to a reflective surface and back to the detector unit, then it should be obvious that radiation from a fire would likewise not pass through these same surfaces and detection would not be possible.

The operation of this device should be obvious to anyone skilled in the art.

The source S is energized through various means which could include automatic switching or manual switching techniques and, if the various surfaces permit the outward transmission of radiation from the source, this radiation will be directed back, upon striking of a reflective surface, to the detector D. If any of these surfaces, such as the lens does not permit this transmission and reflection, then appropriate circuitry may be employed to signal such a fault. This situation is not limited to the lens but includes all the surfaces within the device. Non transmission of radiation may also indicate a fault of the source S or the detector D.

It should be obvious that the applicant has provided a unique unit for the detection of the ability of a radiation detector unit to respond to the presence of radiation and which will monitor the various radiation passing surfaces of the unit to insure the absence of radiation absorbing or blocking materials by determining that these surface areas are capable of radiation transmission in the range of radiation to which the detector is sensitive.

What I claim is:

1. An improvement in radiation detection apparatus, such improvement including:
   a. a longitudinally extending housing;
   b. means for mounting a source of radiation in said housing;
   c. means for mounting a detector of radiation in said housing;
   d. radiation shielding means extending longitudinally within said housing and arranged between said radiation source and said detector means to prevent radiation transmission therebetween within said housing;
   e. radiation transmitting passages provided by said housing and said shielding means for the emission of radiation from said source and the reception of the source radiation by said detector; and,
   f. reflective means positioned adjacent said housing and spaced from said shielding means to receive radiation from said source and reflect the same to said detector, whereby the radiation transmitting passage permitting the reception of radiation by said detector is monitored to determine its ability to transmit radiation to said detector.

2. The structure set forth in claim 1 and said housing extending longitudinally beyond said shielding means, said reflective means being provided by said extending housing portion.

3. The structure set forth in claim 1 and said reflective means being carried by said housing and extending across said radiation transmitting passages.

4. The structure set forth in claim 1 and a lens member arranged in covering relation to said passages and maintaining the radiation shield therebetween.

5. The structure set forth in claim 4 and said shielding member being in radiation shielding position with said lens to maintain the shielded relation between said source and said detector within said housing.

6. The structure set forth in claim 5 and said reflective means being arranged on one side of said lens, said source and detector being arranged interiorly of said housing and on the opposite side of said lens.

7. The structure set forth in claim 1 and said shielding means surrounding one of said source and detector means and extending longitudinally within said housing, one of said radiation transmitting passages being defined interiorly of said shielding member, the other of said passages being defined by the exterior surface of said shielding member and the interior of said housing.

8. The structure set forth in claim 7 and a lens member carried by said housing and forming a radiation blocking seal with said shielding member whereby said lens extends across said radiation transmitting passages.

9. The structure set forth in claim 8 and said reflective means being arranged on one side of said lens, said source and detector being arranged on the other side of said lens.

10. The structure set forth in claim 9 and said housing having a portion extending beyond said lens, said reflective means being arranged on said housing.

11. The structure set forth in claim 10 and said reflective means being arranged on said housing and extending across said transmitting passages.

12. The structure set forth in claim 1 and said source of radiation and said detector of radiation being capable of transmitting and receiving ultraviolet respectively.

13. The structure set forth in claim 1 and said source of radiation and said detector of radiation being capable of transmitting and receiving infrared respectively.

14. The structure set forth in claim 1 and said source of radiation and said detector of radiation being capable of transmitting and receiving visible radiation respectively.

* * * * *